(12) United States Patent
Toyomura et al.

(10) Patent No.: US 10,631,790 B2
(45) Date of Patent: Apr. 28, 2020

(54) VITAL SIGN MEASUREMENT APPARATUS (71) Applicant: NIHON KOHDEN CORPORATION, Tokyo (JP)

(72) Inventors: Kenji Toyomura, Tokyo (JP); Asao Igarashi, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1408 days.

(21) Appl. No.: 13/944,739

(22) Filed: Jul. 17, 2013

(65) Prior Publication Data

US 2014/0031639 A1 Jan. 30, 2014

(30) Foreign Application Priority Data

Jul. 24, 2012 (JP) ................................. 2012-163967

(51) Int. Cl.
*A61B 5/00* (2006.01)
*A61B 5/0205* (2006.01)
(Continued)

(52) U.S. Cl.
CPC ............ *A61B 5/7221* (2013.01); *A61B 5/002* (2013.01); *A61B 5/0205* (2013.01); *A61B 5/044* (2013.01);
(Continued)

(58) Field of Classification Search
CPC ..... A61B 5/7221; A61B 5/002; A61B 5/0205; A61B 5/44; A61B 5/7445
(Continued)

(56) References Cited

U.S. PATENT DOCUMENTS 4,698,746 A 10/1987 Goldstein
5,568,814 A 10/1996 Gallant
(Continued)

FOREIGN PATENT DOCUMENTS

EP 1 010 968 A1 6/2000
EP 2 308 370 A1 4/2011
(Continued)

OTHER PUBLICATIONS

Japanese Office Action for the related Japanese Patent Application No. 2012-163967 dated Oct. 6, 2015.
(Continued)

*Primary Examiner* — Gary Jackson
*Assistant Examiner* — Sebastian X Lukjan
(74) *Attorney, Agent, or Firm* — Pearne & Gordon LLP (57) ABSTRACT

A vital sign measurement apparatus including: an input operation section; a first measurement section capable of measuring first vital signs; first and second operating systems; a first arithmetic processing section that runs on the first operating system and that arithmetically processes the first vital signs on the basis of an input signal from the input operation section, thereby generating a first arithmetically processed signal; a second arithmetic processing section that runs on the second operating system, that is communicable with the first arithmetic processing section, and that generates a second arithmetically processed signal on the basis of the input signal from the input operation section by use of the first arithmetically processed signal transmitted from the first arithmetic processing section; and an output control section that can receive the first and second arithmetically processed signals and that outputs at least one of the received arithmetically processed signals.

16 Claims, 5 Drawing Sheets

(51) Int. Cl.
*A61B 5/044* (2006.01)
*G16H 40/63* (2018.01)

(52) U.S. Cl.
CPC .......... *A61B 5/7445* (2013.01); *A61B 5/0024* (2013.01); *A61B 5/743* (2013.01); *A61B 2560/0266* (2013.01); *A61B 2560/0443* (2013.01); *G16H 40/63* (2018.01)

(58) Field of Classification Search
USPC ........................................................ 600/301
See application file for complete search history.

(56) References Cited

U.S. PATENT DOCUMENTS

| | | | |
|---|---|---|---|
| 5,701,894 | A | 12/1997 | Cherry |
| 5,817,035 | A | 10/1998 | Sullivan |
| 6,159,150 | A * | 12/2000 | Yale .................. A61B 8/00 600/437 |
| 6,245,013 | B1 | 6/2001 | Minoz et al. |
| 6,289,462 | B1 * | 9/2001 | McNabb ............. G06F 21/6218 726/21 |
| 6,547,730 | B1 | 4/2003 | Lin et al. |
| 2002/0077548 | A1 | 6/2002 | Amemiya |
| 2002/0151770 | A1 * | 10/2002 | Noll, III ............... A61B 5/0031 600/300 |
| 2004/0236874 | A1 * | 11/2004 | Largman ................. G06F 21/53 710/8 |
| 2005/0113690 | A1 | 5/2005 | Halmann et al. |
| 2008/0161659 | A1 * | 7/2008 | Reichenberger ..... A61B 5/0002 600/301 |
| 2008/0200310 | A1 | 8/2008 | Tagliabue |
| 2009/0006133 | A1 | 1/2009 | Weinert et al. |
| 2010/0005531 | A1 * | 1/2010 | Largman ................. G06F 21/53 726/24 |
| 2011/0063645 | A1 | 3/2011 | Sugino |
| 2011/0080293 | A1 | 4/2011 | Tanishima et al. |
| 2011/0213222 | A1 * | 9/2011 | Leyde .................. A61B 5/0006 600/301 |
| 2014/0022599 | A1 | 1/2014 | Sugino |
| 2014/0228989 | A1 | 8/2014 | Tagliabue |
| 2015/0347882 | A1 | 12/2015 | Sugino |

FOREIGN PATENT DOCUMENTS

| | | |
|---|---|---|
| JP | 2000-132622 A | 5/2000 |
| JP | 2002-200079 A | 7/2002 |
| JP | 2005-161046 A | 6/2005 |
| JP | 2010-519619 A | 6/2010 |
| JP | 2010-534494 A | 11/2010 |
| JP | 2011-87280 A | 4/2011 |
| JP | 2011-98189 A | 5/2011 |
| JP | 2012-003672 A | 1/2012 |
| WO | 97/17012 A1 | 5/1997 |

OTHER PUBLICATIONS

The extended European Search Report for the related European Patent Application No. 13177395.4 dated Dec. 2, 2013.
Japanese Office Action issued in Patent Application No. 2015-223175 dated Oct. 18, 2016.
Notification of First Office Action issued in Chinese Patent Application No. 201310314347 dated Sep. 5, 2016.
European Office action issued in European Patent Application No. 13 177 395.4 dated Jul. 5, 2017.

* cited by examiner

VITAL SIGN MEASUREMENT APPARATUS

BACKGROUND OF THE INVENTION

The invention relates to a vital sign measurement apparatus intended for detecting vital signs from a subject, performing arithmetic operation of the detected vital signs, and displaying an operation result.

A known vital sign measurement display apparatus (a bedside monitor) measures vital signs of a subject and outputs and displays the thus-measured vital signs as waveform information or numeric information. For instance, Patent Document 1 to be described below discloses a bedside monitor that detects vital signs by means of a vital sign detection section attached to a patient and displays the thus-detected vital signs on a display section. The bedside monitor is capable of displaying on the display section a vital alarm which would be output during anomalies of vital signs or a technical alarm which would be output during anomalies of a vital sign monitor, a measurement sensor, or a measurement environment and also displaying on the display section information about how to deal with the anomalies.

RELATED ART DOCUMENT

Patent Document

[Patent Document 1] JP-2011-098189

However, the related-art bedside monitor often adopts, as an operating software for managing a system, a built-in OS (Operating System) built in the system in order to implement a specific function for measuring predetermined waveform information and predetermined numeric information about vital signs. For this reason, the bedside monitor is superior in terms of stable measurement of predetermined vital signs without freezing the system. However, the bedside monitor lacks of flexibility in view of extension of new capabilities, such as retrofitting analysis application and a hard drive disk (HDD). Likewise, the bedside monitor described in connection with Patent Document 1 also lacks of flexibility in terms of extension of capabilities.

SUMMARY

This invention provides a vital sign measurement apparatus (a bedside monitor) capable of assuring the reliability of measuring operation and flexible extension of measurement capabilities.

It is therefore an aspect of the invention to provide a vital sign measurement apparatus including: an input operation section that enables an operator to perform input operation; a first measurement section capable of measuring first vital signs; a first operating system; a second operating system; a first arithmetic processing section that runs on the first operating system and that arithmetically processes the first vital signs measured by the first measurement section on the basis of an input signal from the input operation section, thereby generating a first arithmetically processed signal; a second arithmetic processing section that runs on the second operating system, that is communicable with the first arithmetic processing section, and that generates a second arithmetically processed signal on the basis of the input signal from the input operation section by use of the first arithmetically processed signal transmitted from the first arithmetic processing section; and an output control section that can receive the first arithmetically processed signal produced by the first arithmetic processing section and the second arithmetically processed signal produced by the second arithmetic processing section and that outputs at least one of the received arithmetically processed signals.

The vital sign measurement apparatus may further comprise a second measurement section that can measure second vital signs, wherein the first arithmetic processing section may arithmetically process the second vital signs measured by the second measurement section on the basis of an input signal from the input operation section, to thus generate a first arithmetically processed signal.

The vital sign measurement apparatus may further comprise a second measurement section that can measure second vital signs, wherein the second arithmetic processing section may arithmetically process the second vital signs measured by the second measurement section on the basis of an input signal from the input operation section, to thus generate a second arithmetically processed signal.

The vital sign measurement apparatus may further comprise an extension processing section that runs on the second operating system and that analyzes or stores at least any one of the first vital signs, the second vital signs, the first arithmetically processed signal, and the second arithmetically processed signal.

The second operating system may be a general purpose operating system.

The first arithmetic processing section may shut off a communication with the second arithmetic processing section when determining that an anomaly occurs in the second operating system in course of the communication with the second arithmetic operating section.

The first arithmetic processing section may generate a first arithmetically processed signal by use of the second arithmetically processed signal transmitted from the second arithmetic processing section.

DETAILED DESCRIPTION OF EMBODIMENTS

Embodiments of a vital sign measurement apparatus of the invention is hereunder described by reference to the accompanying drawings.

Figure 1:
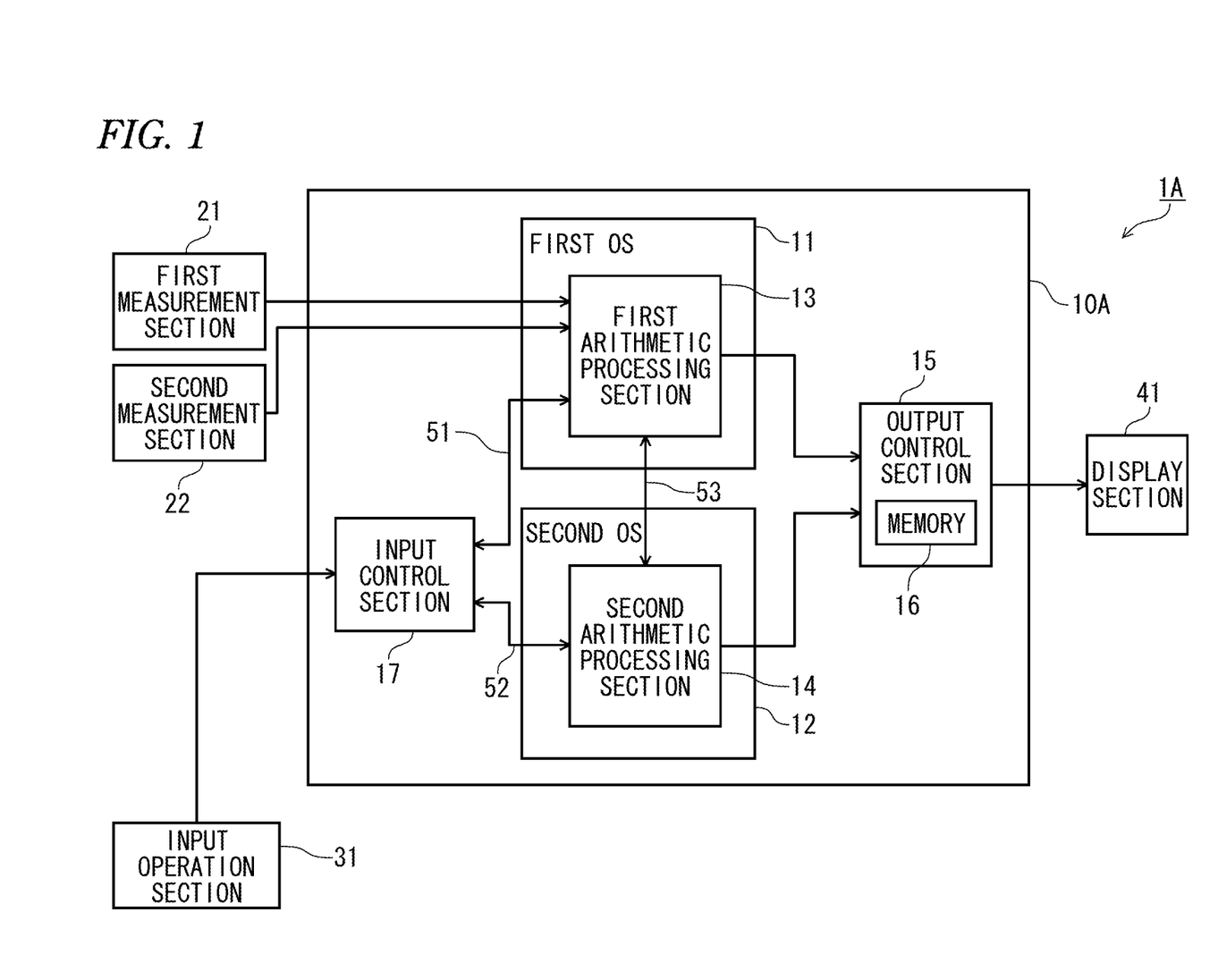
FIG. 1 is a block diagram showing a configuration of a first embodiment of a vital sign measurement apparatus of the invention.

FIG. 1 shows a first embodiment of the vital sign measurement apparatus. A vital sign measurement apparatus 1A refers to an apparatus that is installed for an individual subject and that measures, arithmetically processes, and displays on a screen vital signs (a blood pressure, oxygen saturation, a body temperature, an electrocardiogram, an electroencephalogram, an electromyogram, and others); namely, a so-called bedside monitor. As shown in FIG. 1, the vital sign measurement apparatus 1A has measurement sections (a first measurement section 21 and a second measurement section 22) for measuring vital signs of a subject, an input operation section 31 that receives operation from an operator (a healthcare worker), a vital sign measurement apparatus main body 10A that processes signals (information) input from the measurement sections 21 and 22 and the input operation section 31, and a display section 41 that displays vital signs processed by the vital sign measurement apparatus main body 10A.

The vital sign measurement apparatus main body 10A includes a first operating system (OS: Operating System) 11 and a second operating system 12 that performs basic control and management of a computer, a first arithmetic processing section 13 that runs on the first OS, a second arithmetic processing section 14 that runs on the second OS, an output control section 15 that processes arithmetically processed signals from the first arithmetic processing section 13 and the second arithmetic processing section 14, and an input control section 17 that processes a signal from the input operation section 31.

The first OS 11 is an operating system that provides a control function, a screen display function, a file operation function, and others, of the program. A built-in OS capable of implementing specific functions, such as measuring a vital sign waveform and numeric data pertaining to vital signs of a subject, is adopted for the first OS 11. The built-in OS (hereinafter also called an "embedded OS") is an OS that implements a preset specific function. When compared with a general purpose OS (e.g., Windows, Mac OS, Linux (all of which are registered trademarks) and the like), the embedded OS has a fewer risk of stopping (freezing) processing operation and can implement stable, highly-reliable processing operation. The embedded OS; namely, the first OS 11, is an OS that is adopted for the bedside monitor placed nearby a bed of a subject and, therefore, called a monitor OS.

The second OS 12 is, as in the case with the first OS 11, an operating system that provides a program control function, a screen display function, a file operation function, and the like. However, the general purpose OS (e.g., Windows, Mac OS, Linux (all of which are registered trademarks) and the like) employed in a personal computer (PC) is adopted for the second OS 12. The general purpose OS exhibits a high degree of extension, such as compatibility with a new application, management of a new peripheral device (a device), and Multilanguage operation. Since the general purpose OS; namely, the second OS 12, is an OS that exhibits a high degree of extension, the second OS is also called an extended OS.

The first arithmetic processing section 13 is an arithmetic processing section that runs on the first OS 11. The first arithmetic processing section 13 arithmetically processes vital signs in accordance with a control signal transmitted from the input control section 17. The control signal is one that is based on specifics input by the healthcare worker by way of the input operation section 31. The first arithmetic processing section 13 and the input control section 17 are connected to each other in a communicable manner by means of a bus line 51. The first measurement section 21 for measuring a first vital sign of the subject and the second measurement section 22 for measuring a second vital sign of the subject are connected to the first arithmetic processing section 13. First vital sign information (a vital signal) measured by the first measurement section 21 and second vital sign information (a vital signal) measured by the second measurement section 22 are input to the first arithmetic processing section 13. In accordance with the control signal from the input control section 17, the first arithmetic processing section 13 arithmetically processes the vital sign signal. The number of measurement sections to be connected is not limited to that mentioned in connection with the embodiment and can be determined in accordance with the number of vital signs of the subject needed to be measured. The first arithmetic processing section 13 can arithmetically process a plurality of vital signs (vital signals), thereby generating and outputting an arithmetically processed signal (a first arithmetically processed signal).

The first arithmetic processing section 13 measures various types of numeric data (a blood pressure value, a body temperature, an oxygen concentration, a concentration of carbon dioxide, a cardiac output, and others) pertaining to the vital sign signals received from the measurement sections 21 and 22. Further, the first arithmetic processing section 13 prepares a list and a graph of measured values on the basis of the measured numeric data or determines whether or not a measured value is an anomaly (a value exceeding a preset threshold value) and generates an alarm (warning) sign when the measured value is determined to be an anomalous value. The first arithmetic processing section 13 outputs to the output control section 15, as an arithmetically processed signal (a first arithmetically processed signal), a signal pertaining to a vital sign waveform, various types of numeric data, a list and a graph of measured values, and an anomaly warning sign. The first arithmetic processing section 13 memorizes and stores in storage means (memory), which are omitted from illustrations, the arithmetically processed signal (the first arithmetically processed signal) and data received from the first measurement section 21, the second measurement section 22, the input control section 17, and the second arithmetic processing section 14.

The vital sign signals that are input to the first arithmetic processing section 13 and measured by the first measurement section 21 and the second measurement section 22 are, in many cases, of types that are measured without interruption all the time on the patient by means of the bedside monitor. Therefore, stable vital signs can be obtained without interruption by letting the first arithmetic processing section 13 that processes the vital sign signals run on the monitor OS (i.e., the first OS 11) that exhibits high reliability in processing operation.

The second arithmetic processing section 14 is an arithmetic processing section that runs on the second OS 12. The second arithmetic processing section 14 arithmetically processes vital signs in accordance with a control signal transmitted from the input control section 17. The control signal is one that is based on specifics input by the healthcare worker by way of the input operation section 31. The second arithmetic processing section 14 and the input control section 17 are connected to each other in a communicable way by means of a bus line 52.

The second arithmetic processing section 14 is additionally connected in a communicable manner to the first arithmetic processing section 13 by means of a bus line 53. An arithmetically processed signal (a second arithmetically processed signal) that is arithmetically processed by the second arithmetic processing section 14, the control signal transmitted from the input control section 17 to the second arithmetic processing section 14, vital sign signals input from the measurement sections 21 and 22 to the first arithmetic processing section 13, the arithmetically processed signal (the first arithmetically processed signal) that is arithmetically processed by the first arithmetic processing section 13, and the control signal transmitted from the input control section 17 to the first arithmetic processing section 13 are exchanged between the second arithmetic processing section 14 and the first arithmetic processing section 13 by way of the bus line 53.

Upon detection of cessation (an anomalous state, like a frozen state) of the second OS 12 (the general purpose OS) in a communication with the second arithmetic processing section 14 by way of the bus line 53, the first arithmetic processing section 13 can perform processing for making sparse the communication with the second arithmetic processing section 14 (or partially blocking the communication) that is established by way of the bus line 53 so that the first arithmetic processing section 13 is prevented from being affected by cessation. Alternatively, the first arithmetic processing section 13 can also perform processing for making sparse the communication with the second arithmetic processing section 14 that is established by way of the bus line 53 so that the communication is protected against influence of a failure of a part, or the like.

The second arithmetic processing section 14 arithmetically processes the arithmetically processed signal (the first arithmetically processed signal) transmitted from the first arithmetic processing section 13 in accordance with the control signal transmitted from the input control section 17, thereby generating and outputting an arithmetically processed signal (the second arithmetically processed signal) to the output control section 15. The second arithmetic processing section 14 memorizes and stores the thus-generated arithmetically processed signal (the second arithmetically processed signal) and data received from the input control section 17 and the first arithmetic processing section 13 in the storage means omitted from the illustrations (memory, an HDD, and the like). Since the second arithmetic processing section 14 runs on an extended OS (the second OS 12) exhibiting high extendability and high versatility, displaying a vital sign analysis graph, statistical data processing, multi-language compatible processing, and advanced graphic processing, like an embellished screen, can be performed by use of a highly advanced function that cannot be processed by means of the embedded OS (the first OS 11) and by analysis of the arithmetically processed signal transmitted from the first arithmetic processing section 13.

The output control section 15 is made up of a graphic chip (a video chip) that is an integrated circuit which performs image processing. The output control section 15 can simultaneously receive a plurality of signals. As shown in FIG. 1, the output control section 15 receives the arithmetically processed signal (the first arithmetically processed signal) generated by the first arithmetic processing section 13 and the arithmetically processed signal (the second arithmetically processed signal) generated by the second arithmetic processing section 14. The output control section 15 performs control processing for outputting the received arithmetically-processed signal to the display section 41 and processing for preparing rewritten data pertaining to an image to be displayed on the display section 41 and displaying, in an overlapping manner (an overlap between front and back display positions), a plurality of types of screens (windows) to be displayed on the display section 41.

The output control section 15 can also output both received arithmetically processed signals; namely, the first arithmetically processed signal and the second arithmetically processed signal, or select and output any one of them. Moreover, when the received signal is only one arithmetically processed signal; namely, either the first arithmetically processed signal or the second arithmetically processed signal, the output control section 15 can also output only an arithmetically processed signal being received. When received both of the arithmetically processed signals, or the first arithmetically processed signal and the second arithmetically processed signal, the output control section 15 performs processing for determining front and back window display positions in order to display data pertaining to the arithmetically processed signals on two different screens (windows) in an overlapping manner. Processing for displaying windows at front and back positions is carried out on the basis of a command signal input by the healthcare worker by way of the input operation section 31. In order to display an image of a measured vital sign on the display section 41, the output control section 15 memorizes and stores received data pertaining to the first arithmetically processed signal and the second arithmetically processed signal as rewritten data for the image in memory 16 provided in the output control section 15.

The input control section 17 is connected to the input operation section 31 and performs processing for converting an operation signal input from the input operation section 31 into a control signal for controlling the first arithmetic processing section 13 and the second arithmetic processing section 14. The input control section 17 is connected in a communicable manner to the second arithmetic processing section 14 by way of the bus line 52 as well as to the first arithmetic processing section 13 by way of the bus line 51. The input control section 17 transmits the control signal into which the operation signal is converted to the first arithmetic processing section 13 and the second arithmetic processing section 14 and receives an answer signal and a command signal transmitted from the first arithmetic processing section 13 and the second arithmetic processing section 14.

The control signal transmitted from the input control section 17 to the first arithmetic processing section 13 includes the followings; for instance, a control signal for commanding which one of vital sign signals measured by the measurement sections is output as an arithmetically processed signal, a control signal for setting a preset value, like a threshold value and sensitivity of a vital sign signal, a control signal for specifying a type of an alarm (warning) sign, a control signal for ceasing and deleting the alarm (warning) sign, and a control signal for issuing a command to the effect that the communication with the second arithmetic processing section 14 should be interrupted or resumed.

The control signal transmitted from the input control section 17 to the second arithmetic processing section 14 includes the followings; for instance, a control signal for commanding that the arithmetically processed signal (the first arithmetically processed signal) received from the first arithmetic processing section 13 should be analyzed and arithmetically processed to thereby generate another arithmetically processed signal (the second arithmetically processed signal), a control signal for controlling operation of the first arithmetic processing section 13 by way of the bus line 53, and a control signal for command that the communication with the first arithmetic processing section 13 should be shut off or resumed. Incidentally, the control signal for controlling the operation of the first arithmetic processing section 13 by way of the bus line 53 is analogous to specifics of the control signal transmitted from the input control section 17 to the first arithmetic processing section 13.

A signal that the input control section 17 receives from the first arithmetic processing section 13 includes the followings; for instance, a signal for notifying that the first arithmetic processing section 13 has detected the second OS 12 in an inactive (frozen) state by means of the communication with the second arithmetic processing section 14 by way of the bus line 53 and a signal for commanding that whether to transmit the control signal to be transmitted from the input control section 17 by way of the bus line 51 or the bus line 52. Moreover, a signal that the input control section 17 receives from the second arithmetic processing section 14 includes; for instance, a signal for notifying that the second arithmetic processing section 14 has received the arithmetically processed signal (the first arithmetically processed signal) from the first arithmetic processing section 13 by way of the bus line 53.

When the second OS (the general purpose OS) 12 is in normal operation (a non-frozen state), the input control section 17 transmits a control signal showing specifics of operation input from the input operation section 31 to the second arithmetic processing section 14 by way of the bus line 52. The control signal transmitted to the second arithmetic processing section 14 is additionally transmitted from the second arithmetic processing section 14 to the first arithmetic processing section 13 by way of the bus line 53.

In contrast, when the second OS 12 or the second arithmetic processing section 14 becomes inoperative (frozen), the input control section 17 transmits the control signal to the first arithmetic processing section 13 by way of the bus line 51. In this case, in accordance with an anomaly detection signal transmitted from the first arithmetic processing section 13, the input control section 17 detects that the second OS 12 or the second arithmetic processing section 14 became frozen. The first arithmetic processing section 13 detects an anomalous state of the second arithmetic processing section 14; namely, a frozen state of the second OS 12 or the second arithmetic processing section 14 on the basis of specifics of the communication with the second arithmetic processing section 14 established by way of the bus line 53, transmitting to the input control section 17 by way of the bus line 51 a signal to the effect that the anomalous state (the anomaly detection signal) is detected. The input control section 17 received the signal performs switching processing so as to stop the control signal that is being transmitted from the input control section 17 to the second arithmetic processing section 14 and transmit the control signal to the first arithmetic processing section 13 by way of the bus line 51. Moreover, in order to prevent influence of the frozen state in which the second OS 12 or the second arithmetic processing section 14 is now in, the first arithmetic processing section 13 is at this time processing for making sparse (or shutting off) the communication with the second arithmetic processing section 14 established by way of the bus line 53.

The first measurement section 21 and the second measurement section 22 are measurement sections that measure vital signs of the subject and connected to the first arithmetic processing section 13 in the embodiment. The first measurement section 21 and the second measurement section 22 convert vital sign information collected from the subject into an electric signal and input the thus-converted electric signal to the first arithmetic processing section 13. Each of the first measurement section 21 and the second measurement section 22 is equipped with electrodes or various sensors to be attached to or inserted into the subject. In FIG. 1, two measurement sections are connected. However, the minimum requirement is that the number of measurement sections to be connected be determined in accordance with the number of types of vital signs to be measured. Types of vital signs to be measured include; for instance, a blood pressure value, a body temperature, an oxygen concentration, a concentration of carbon dioxide, a cardiac output, and others.

The input operation section 31 is for manipulating operation settings of the vital sign measurement apparatus main body 10A and receives an operation input performed by the operator (the healthcare worker). The input operation section 31 can be made up of a keyboard, a mouse, a touch panel, or the like. Specifics of operation include selecting and setting vital signs (a vital sign waveform, numeric data, a graph, and the like) to be displayed on the display section 41, selecting and setting an arithmetically processed signal (the first or second arithmetically processed signal) output from the output control section 15, and setting a threshold value for each of vital signs, setting indication and cancellation of an alarm (warning) sign. Enumerated as an example of the input operation section 31 is a keyboard, a mouse, or a touch panel. However, the input operation section 31 is not limited to them. The essential requirement for the input operation section 13 is that any element is acceptable, so long as the element assumes, as a man-machine interface, a mode for accepting an operation input made by the operator.

The display section 41 is for displaying vital signs (a vital sign waveform, numeric data, a graph, and the like) under control of the output control section 15. Under control of the output control section 15, there can be displayed vital signs pertinent to both or either the first arithmetically processed signal output from the first arithmetic processing section 13 or the second arithmetically processed signal output from the second arithmetic processing section 14.

The vital sign measurement apparatus 1A of the first embodiment of the invention has a configuration, such as that mentioned above, and yields the following working effects.

The vital sign measurement apparatus 1A has the first arithmetic processing section 13 that runs on the first OS (the embedded OS) 11 to thereby perform operation processing in accordance with setting conditions input by the operator (the healthcare worker) and the second arithmetic processing section 14 that runs on the second OS (the general purpose OS) 12 to thereby perform operation processing in accordance with setting conditions input by the operator (the healthcare worker). The output control section 15 of the vital sign measurement apparatus 1A can output at least any one of the arithmetically processed signals received from the first arithmetic processing section 13 and the second arithmetic processing section 14. Therefore, even when one of the OSs or one of the arithmetic processing sections becomes inoperative; for instance, even when the general purpose OS or the second arithmetic processing section 14 becomes frozen, the vital sign measurement apparatus 1A can measure and arithmetically process vital signs without interruption by means of the first arithmetic processing section 13 that runs on the other OS, or the embedded OS. The arithmetically processed vital signs can be output from the output control section 15 without being affected by the cessation of the general purpose OS. As a matter of course, when the vital signs are output, the output can also be along with an embellished image.

In addition to outputting and displaying the first arithmetically processed signal generated by the first arithmetic processing section 13 that runs on the first OS (the embedded OS) 11, the vital sign measurement apparatus 1A can output and display the second arithmetically processed signal that is generated by means of the second arithmetic processing section 14 that runs on the second OS (the general purpose OS) 12 analyzing and arithmetically processing the first arithmetically processed signal generated by the first arithmetic processing section 13. Consequently, the vital sign measurement apparatus 1A can stably output and display, by means of the first OS, the vital signs that need to be output and displayed without interruption at all times and also output and display, by means of the second OS, vital signs that require more advanced analytical capabilities and are abound in analytical types.

The input control section 17 is connected in a communicable way to the first arithmetic processing section 13 by way of the bus line 51 and to the second arithmetic processing section 14 by way of the bus line 52. Therefore, even if the second arithmetic processing section 14 becomes inoperative as a result of the second OS (the general purpose OS) 12 or the second arithmetic processing section 14 being frozen, the control signal from the input control section 17 can be transmitted to the first arithmetic processing section 13 by way of the bus line 51. Consequently, the vital sign measurement apparatus main body 10A can output a signal pertinent to the vital signs arithmetically processed by the first arithmetic processing section 13 (the first arithmetically processed signal) without being affected by the cessation of the second OS 12 according to the preset conditions input by way of the input operation section 31, so that the vital signs measured on the subject can be stably, continually displayed on the display section 41.

According to the preset conditions input by way of the input operation section 31, the first arithmetic processing section 13 can receive a plurality of vital signs (a vital signal) in accordance with the number of vital signs that need to be measured on the subject, arithmetically process the thus-received signal to thereby generate the arithmetically processed signal (the first arithmetically processed signal), and output the thus-produced signal. The display section 41 hence can output and display a plurality of vital signs without interruption at all times.

A graphic chip (a video chip) capable of receiving a plurality of video signals at a time is used for the output control section 15. The output control section 15 can receive the first arithmetically processed signal generated by the first arithmetic processing section 13 and the second arithmetically processed signal generated by the second arithmetic processing section 14 or can receive any one of the arithmetically processed signals. Further, a received arithmetically processed signal can also be selected and output. Consequently, even when the second arithmetically processed signal is not input to the output control section 15 as a result of the second OS 12 (the general purpose OS) or the second arithmetic processing section 14 being frozen, the vital sign measurement apparatus 1A can stably output, from the output control section 15, the first arithmetically processed signal received from the first arithmetic processing section 13 without interruption and being affected by the failure (the state of cessation) of the general purpose OS. Therefore, vital signs of the subject that need to be observed at all times can be displayed on the display section 14 without interruption.

Further, upon detection of cessation (freezing) of the second OS 12 (the general purpose OS) in the communication with the second arithmetic processing section 14 by way of the bus line 53, the first arithmetic processing section 13 can perform processing for making sparse (or blocking at least a portion of) the communication with the second arithmetic processing section 14 by way of the bus line 53. Alternatively, the first arithmetic processing section 13 can also perform processing for making sparse the communication with the second arithmetic processing section 14 by way of the bus line 53 such that communication is protected from the influence of the failure, such as a failure of a part. By means of the configuration, the vital sign measurement apparatus 1A can prevent the first OS 11 from being affected by cessation of the second OS 12 and stably output the first arithmetically processed signal without interruption from the first arithmetic processing section 13.

In addition to including the first OS (the embedded OS) 11, the vital sign measurement apparatus 1A adopts the general purpose OS (e.g., Windows, Mac OS, Linux (all of which are registered trademarks) and the like) as the second OS 12. Accordingly, extension of capabilities, like addition of a graph display, statistical processing of measured data, advanced graphic processing like an embellished screen, an increase in the number of compatible languages, can also be flexibly, easily implemented by addition of new application software. A new peripheral device can also be controlled by incorporation of a device driver. Furthermore, the vital sign measurement apparatus 1A also exhibits extendability, such as easy addition of an HDD.

Figure 2:
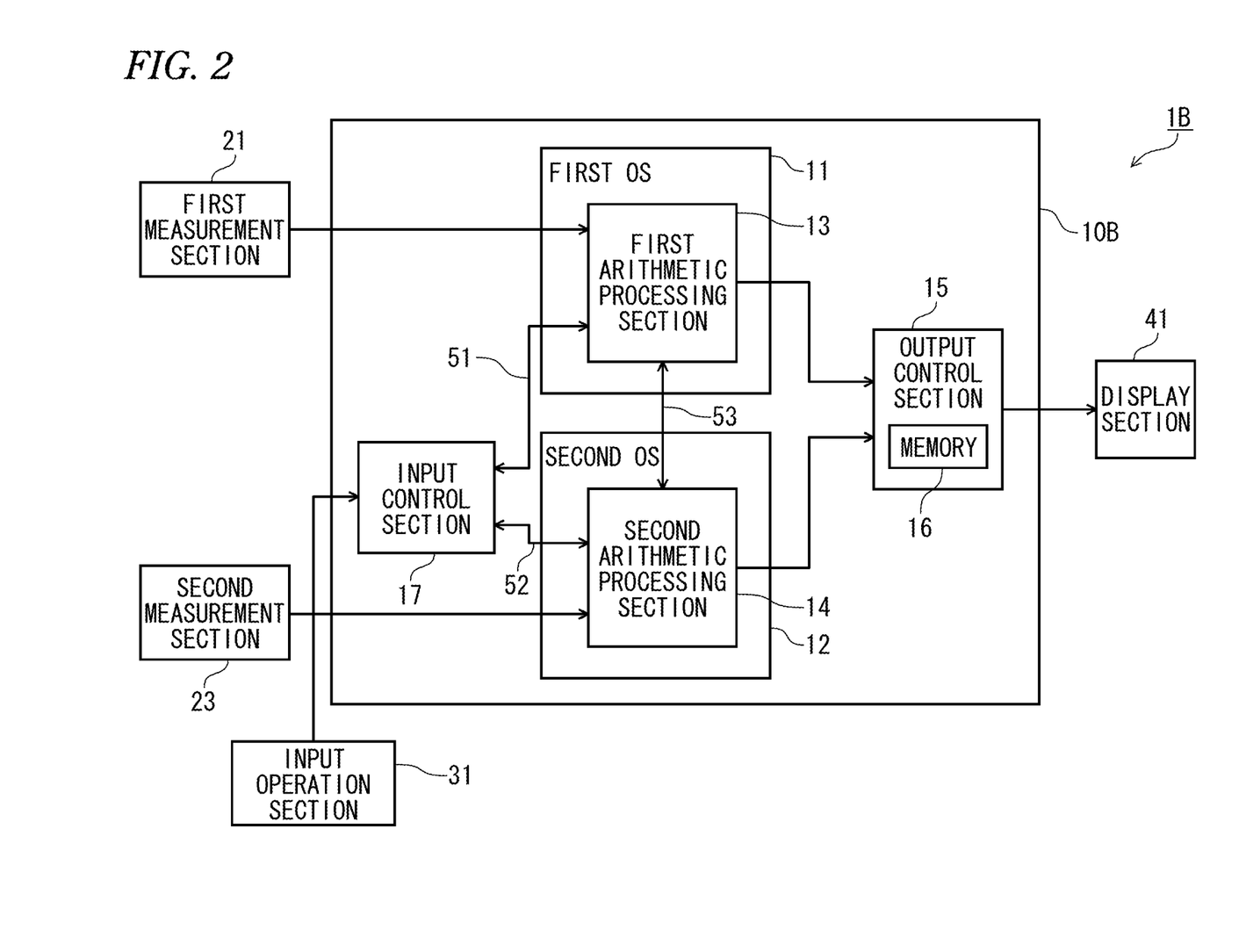
FIG. 2 is a block diagram showing a configuration of a second embodiment of a vital sign measurement apparatus of the invention.

FIG. 2 shows a second embodiment of the vital sign measurement apparatus. A vital sign measurement apparatus 1B differs from the vital sign measurement apparatus 1A described in connection with the first embodiment in that the signals patient to the vital signs measured by the measurement sections are input not only to the first arithmetic processing section 13 but also to the second arithmetic processing section 14. Although the vital sign measurement apparatus 1B is hereunder described, elements that are identical with or analogous to their counterpart elements described in connection with the vital sign measurement apparatus 1A are given the same reference numerals, and the elements can yield working effects similar to those yielded by their counterpart elements of the vital sign measurement apparatus 1A. Further, explanations about the elements are also analogous.

The first arithmetic processing section 13 is an arithmetic processing section that runs on the first OS (the embedded OS) 11 and arithmetically processes vital signs in accordance with the control signal transmitted from the input control section 17. The control signal is one that is based on operation details input by the healthcare worker by way of the input operation section 31. The first arithmetic processing section 13 and the input control section 17 are connected in a communicable manner by way of the bus line 51. The first measurement section 21 for measuring the first vital signs of the subject is connected to the first arithmetic processing section 13. The first vital signs (the vital signal) measured by the first measurement section 21 are input to the first arithmetic processing section 13. The first arithmetic processing section 13 arithmetically processes the first vital signal on the basis of the control signal from the input control section 17, generating and outputting the first arithmetically processed signal.

The first arithmetic processing section 13 memorizes and stores the thus-generated first arithmetically processed signal and data received from the first measurement section 21, the input control section 17, and the second arithmetic processing section 14 in the storage means (memory) that is omitted from the illustrations. The number of measurement sections to be connected to the first arithmetic processing section 13 is not limited to the number described in connection with the embodiment and can be determined in accordance with the number of types of vital signs that need to be measured on the subject. For instance, in addition to the first measurement section 21, a plurality of measurement sections, like a third measurement section and a fourth measurement section, can be connected to the first arithmetic processing section 13.

The second arithmetic processing section 14 is an arithmetic processing section that runs on the second OS (the general purpose OS) 12 and arithmetically processes the vital signs in accordance with the control signal transmitted from the input control section 17. The control signal is one that is based on operations input by the healthcare worker by way of the input operation section 31. The second arithmetic processing section 14 and the input control section 17 are connected in communicable manner to each other by means of the bus line 52. A second measurement section 23 for measuring second vital signs of the subject is connected to the second arithmetic processing section 14. The second vital signs (the vital signal) measured by the second measurement section 23 are input to the second arithmetic processing section 14. The second arithmetic processing section 14 arithmetically processes the second vital signal in accordance with the control signal from the input control section 17, generating and outputting the second arithmetically processed signal. The number of measurement sections to be connected to the second arithmetic processing section 14 is not limited to the number described in connection with the embodiment and can be determined in accordance with the number of types of vital signs that need to be measured on the subject. For instance, in addition to the second measurement section 23, a plurality of measurement sections, like a fifth measurement section and a sixth measurement section, can be connected to the second arithmetic processing section 14.

The vital signs (the vital signal) to be measured by the second measurement section 23 include; for instance, an electrocardiogram signal, an electroencephalogram signal or a signal pertinent to an electroencephalogram test, an electromyogram signal, an evoked potential signal, and the like, that are obtained not by continual, constant measurement but by periodic measurement carried out for; for instance, tens of minutes.

An electrocardiogram signal is derived by electrocardiogram electrodes put on four limbs and a chest of a living body. The thus-derived electrocardiogram signal is input to the second arithmetic processing section 14, and the second arithmetic processing section 14 performs arithmetic processing, like collection, measurement, and analysis of data.

The signal pertinent to the electroencephalogram or the electroencephalogram test is derived by means of electrodes, various sensors, or the like. The signal pertinent to the electroencephalogram test includes an electrocardiographic waveform, an electromyogram waveform, a respiratory waveform, ocular movements, an oxygen saturation, a concentration of carbon dioxide, and the like. The thus-derived signal is input to the second arithmetic processing section 14, and the second arithmetic processing section 14 performs arithmetic processing, such as collection, measurement, and analysis of data. The measurement section of the first arithmetic processing section 13 can measure, among the signals pertinent to the electroencephalogram test, a signal that can be measured by the measurement section connected to the first arithmetic processing section 13, and the thus-measured signal can be transmitted from the first arithmetic processing section 13 to the second arithmetic processing section 14.

Signals pertinent to the electromyogram and the evoked potential are derived by means of various electrodes. The thus-derived signals pertinent to the electromyogram and the evoked potentials (i.e., a waveform and a measured value) are input to the second arithmetic processing section 14, and the second arithmetic processing section 14 performs arithmetic processing, like collection, measurement, and analysis of data.

The second arithmetic processing section 14 generates and outputs the second arithmetically processed signal, and memorizes and stores the thus-generated second arithmetically processed signal and the data received from the second measurement section 23, the input control section 17, and the first arithmetic processing section 13 in the storage means omitted from the illustrations (memory, an HDD, and the like). The output second arithmetically processed signal is input to the output control section 15 and subsequently displayed as an image on the display section 41. As mentioned above, as a result of adoption of the second OS 12 (the general purpose OS), the vital sign measurement apparatus (the bedside monitor) 1B can be operated as a measurement apparatus with capabilities that are equivalent to those of cardiography equipment, electroencephalogram equipment, and an electromyogram/evoked potential tester that are custom-designed inspection devices, by means of only connecting the second measurement section 23 to the second arithmetic processing section 14.

The second arithmetic processing section 14 is additionally connected in a communicable manner to the first arithmetic processing section 13 by means of the bus line 53. The second arithmetically processed signal that is arithmetically processed by the second arithmetic processing section 14, the vital signal input from the second measurement section 23 to the second arithmetic processing section 14, the control signal transmitted from the input control section 17 to the second arithmetic processing section 14, the first arithmetically processed signal that is arithmetically processed by the first arithmetic processing section 13, the vital signal input from the first measurement section 21 to the first arithmetic processing section 13, and the control signal transmitted from the input control section 17 to the first arithmetic processing section 13 are exchanged between the second arithmetic processing section 14 and the first arithmetic processing section 13 by way of the bus line 53.

The second arithmetic processing section 14 can also generate the second arithmetically processed signal, by use of the first arithmetically processed signal transmitted from the first arithmetic processing section 13 by way of the bus line 53 in accordance with the control signal transmitted from the input control section 17. The second arithmetic processing section 14 outputs the thus-generated second arithmetically processed signal to the output control section 15, and memorizes and stores the second arithmetically processed signal into storage means omitted from the illustrations (memory, an HDD, and the like).

In accordance with the control signals (including a control signal transmitted by way of the bus lines 52 and 53 (or the second arithmetic processing section 14) as well as a control signal transmitted by way of the bus line 51) transmitted from the input control section 17, the first arithmetic processing section 13 can also generate the first arithmetically processed signal by use of the second arithmetically processed signal that is transmitted from the second arithmetic processing section 14 by way of the bus line 53 and arithmetically generated by the second arithmetic processing section 14 and the vital signal that is transmitted from the second arithmetic processing section 14 and measured by the second measurement section 23. The first arithmetic processing section 13 outputs the thus-generated first arithmetically processed signal to the output control section 15 and memorizes and stores the signal into storage means (memory) that is omitted from the drawings.

The vital sign measurement apparatus 1B of the second embodiment has the configuration, such as that mentioned above, thereby yielding the following working effects as well as yielding the working effects yielded by the vital sign measurement apparatus 1A of the first embodiment.

Since the vital sign measurement apparatus 1B adopts the second OS (the general purpose OS) 12, the vital sign measurement apparatus 1B can measure vital signs as an apparatus having measurement capabilities equivalent to cardiography equipment, electroencephalogram equipment, and an electromyogram/evoked potential tester, by means of only connecting the second measurement section 23 (a compact measurement input section equipped with the electrodes, various sensors, and the like) to the second arithmetic processing section 14 without bringing into a patient room a related-art, large-size custom-designed examination apparatus, such as an electroencephalograph, cardiography equipment, and an electromyogram. Therefore, even when a clinical site is narrow, the bedside monitor can be operated concurrently as a more accurate measurement apparatus. A quick and reliable diagnosis can be performed by means of one apparatus.

Figure 3:
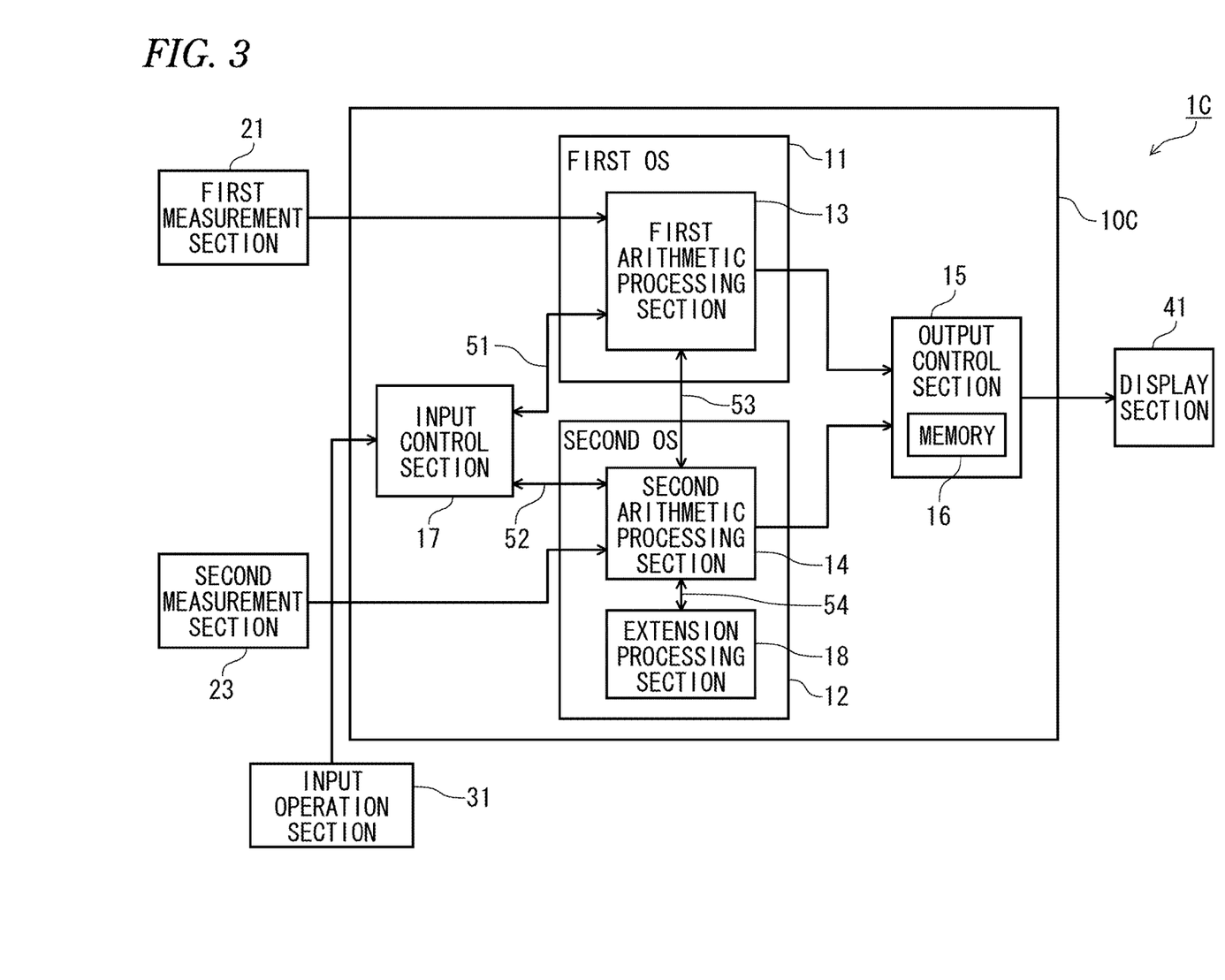
FIG. 3 is a block diagram showing a configuration of a third embodiment of a vital sign measurement apparatus of the invention.

FIG. 3 shows a third embodiment of the vital sign measurement apparatus. A vital sign measurement apparatus 1C differs from the vital sign measurement apparatus 1A of the first embodiment in that vital signs (the vital signal) measured by the measurement section are input to the second arithmetic calculation section 14 as well as to the first arithmetic calculation section 13. The configuration is analogous to the configuration of the vital sign measurement apparatus 1B (see FIG. 2) of the second embodiment. The vital sign measurement apparatus 1C differs from the vital sign measurement apparatus 1A of the first embodiment in that the vital sign measurement apparatus 1C has an extension processing section 18 that runs on the second OS 12. Although the vital sign measurement apparatus 1C is hereunder described, elements that are identical with or analogous to those of the counterpart elements of the vital sign measurement apparatus 1A and the vital sign measurement apparatus 1B are assigned the same reference numerals. The elements can yield the working effects analogous to those yielded by the elements of the vital sign measurement apparatus 1A and the elements of the vital sign measurement apparatus 1B. Explanations about their elements are also analogous.

The extension processing section 18 is a processing section that runs on the second OS (the general purpose OS) 12 and performs extended processing; namely, arithmetic processing of the vital signs in accordance with the control signal transmitted from the input control section 17. The control signal is a signal based on specifics input by the healthcare worker by way of the input operation section 13. The extension processing section 18 and the second arithmetic processing section 14 are connected in communicable manner to each other by means of a bus line 54. The second arithmetic processing section transmits to the extension processing section 18 by way of the bus line 54 the vital sign signal received from the first arithmetic processing section 13 by the first measurement section 21, the vital sign signal received from the second measurement section 23, the first arithmetically processed signal that is received from the first arithmetic processing section 13 and generated by the first arithmetic processing section 13, and the second arithmetically processed signal generated by the second arithmetic processing section 14. The extension processing section 18 can perform extension processing, such as analysis or saving of the signal received from the second arithmetic processing section 14 and transmit the thus-generated extension signal processing to the second arithmetic processing section 14.

The second arithmetic processing section 14 can also output the extension processing signal received from the extension processing section 18 to the output control section 15. The second arithmetic processing section 14 memorizes and stores the received extension processing section into storage means (memory, an HDD, or the like) that is omitted from the illustrations.

In addition to yielding the working effects yielded by the vital sign measurement apparatus 1A of the first embodiment and the vital sign measurement apparatus 1B of the second embodiment, the vital sign measurement apparatus 1C of the third embodiment further yields the following working effects by means of having a configuration, such as that mentioned above.

The vital sign measurement apparatus 1C can easily perform update processing intended for increasing the number of compatible languages, saving operation for the purpose of backing up or archiving measured data, such as management of and response to a new device, and experimental addition/extension of new analytical capabilities by means of letting the extension processing section 18 having an extension capability run on the second OS (the general purpose OS) 12.

Figure 4:
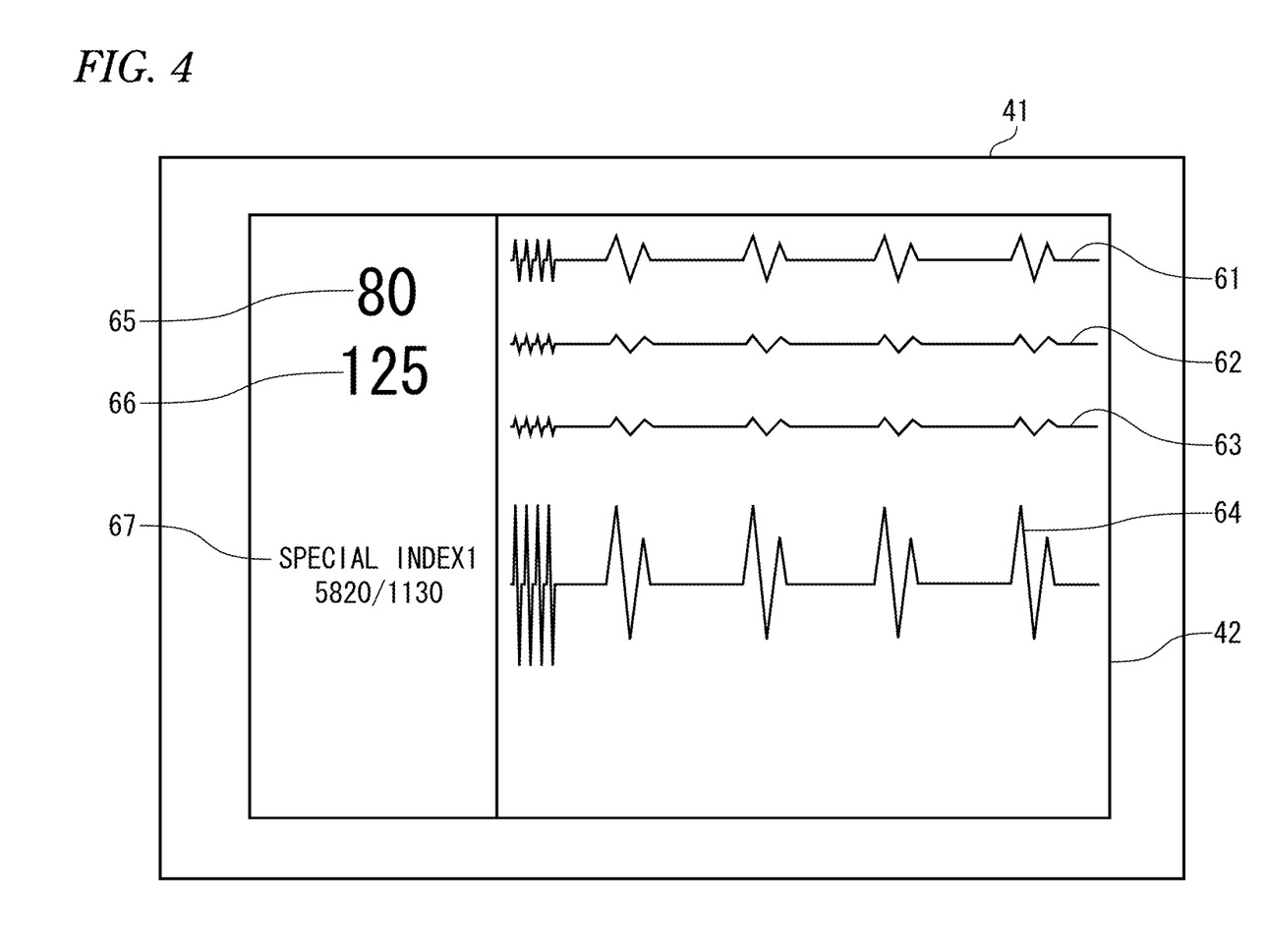
FIG. 4 is a chart showing a vital sign waveform and numeric data based on a first arithmetically processed signal and a second arithmetically processed signal that are displayed on a display section.
Figure 5:
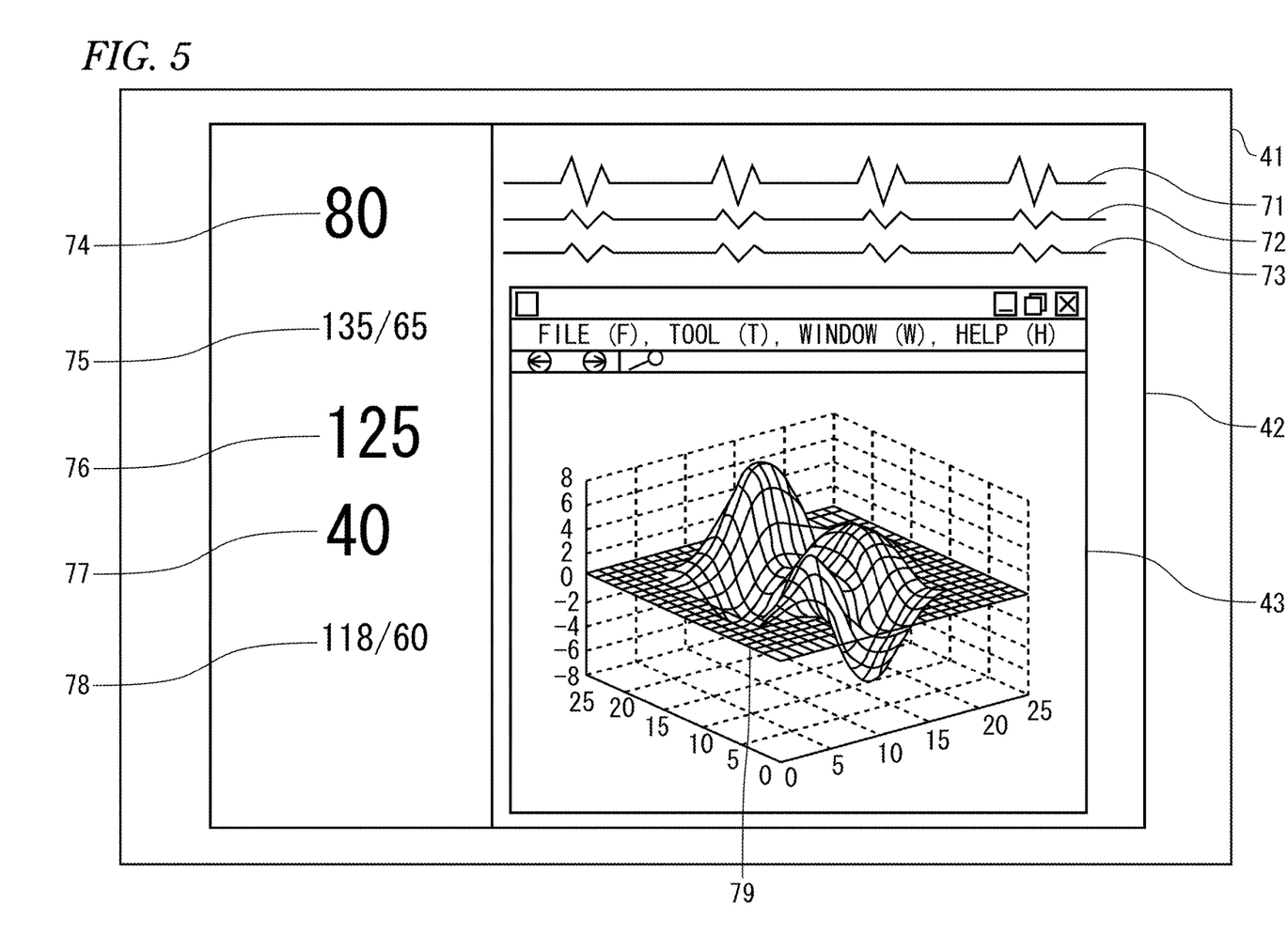
FIG. 5 is an illustration showing the vital sign waveform an the numeric data that are based on the first arithmetically processed signal displayed on the display section and a vial sign analysis graph based on the second arithmetically processed signal.

FIGS. 4 and 5 show respective forms of vital signs (a vital sign waveform, numeric data, a vital sign analytical graph, and the like) to be displayed on the display section 41. Vital signs that are displayed on the display section 41 are hereunder described in correspondence with FIG. 1.

First, FIG. 4 shows that vital sign waveforms 61 to 64 and numeric data 65 to 67 corresponding to the vital sign waveforms are displayed on a display screen (window) 42 of the display section 41. The vital sign waveforms 61 to 63 are measured by the three measurement sections and show waveforms of vital signs arithmetically processed by the first arithmetic processing section 13. The vital sign waveforms 64 show waveforms that are generated by arithmetically processing the vital sign waveforms 61 to 63 by means of the second arithmetic processing section 14. The numeric data 65 and 66 represent as numeric data any of the vital sign waveforms 61 to 63, showing; for instance, a cardiac rate and a blood pressure value. The numeric data 67 display the vital sign waveform 64 as numeric data.

The vital signs measured by the three measurement sections are input to the first arithmetic processing section 13. The first arithmetic processing section 13 arithmetically processes the vital signs to thereby generate the first arithmetically processed signal and transmits the thus-generated first arithmetically processed signal to the output control section 15. The first arithmetically processed signal generated by the first arithmetic processing section 13 corresponds to a signal pertinent to the vital sign waveforms 61 to 63 and the numeric data 65 and 66.

The first arithmetic processing section 13 transmits the thus-generated first arithmetically processed signal to the second arithmetic processing section 14. The second arithmetic processing section 14 subjects the thus-received first arithmetically processed signal to numerical analysis processing, thereby generating a second arithmetically processed signal and transmitting the thus-generated second arithmetically processed signal to the output control section 15. The second arithmetically processed signal generated by the second arithmetic processing section 13 corresponds to a signal pertinent to the vital sign waveform 64 and the numeric data 67.

The output control section 15 performs control operation such that the first arithmetically processed signal and the second arithmetically processed signal thus received are displayed on the single window 42 of the display section 41. The displayed vital sign waveforms 61 to 63 and the numeric data 65 and 66 are monitoring data to be measured at all times. The monitoring data are output from the first arithmetic processing section 13 that runs on the first OS (embedded OS) 11, whereby the monitoring data can be continually displayed on the display section 41 without interruption and without being affected by the operating state of the second OS (the general purpose OS) 12. Moreover, Since the second arithmetic processing section 14 runs on the second OS (the general purpose OS) 12 that exhibits high extendability, the first arithmetically processed signal is additionally arithmetically processed by the second arithmetic processing section 14, so that vital signs that exhibit a higher degree of analysis accuracy can be displayed on the display section 41.

Subsequently, FIG. 5 shows vital sign waveforms 71 to 73 and numeric data 74 to 78 on the display screen (window) 42 of the display section 41. A vital sign analysis graph 79 is displayed on another window 43 that is different from the window 42. The vital sign waveforms 71 to 73 displayed on the window 42 show waveforms of vital signs that are measured by the three measurement sections and that are arithmetically processed by the first arithmetic processing section 13. The numeric data 74 to 78 displayed on the window 42 show as numeric data numeric data measured by the measurement sections and the vital sign waveforms 71 to 73. The vital sign analysis graph 79 displayed on the window 43 represents a graph produced by arithmetically processing the vital sign waveforms 71 to 73 and the numeric data 74 to 78 with the second arithmetic processing section 14. The window 43 is displayed in a pop-up manner on the window 42.

The vital signs measured by the measurement section are input to the first arithmetic processing section 13. The first arithmetic processing section 13 arithmetically processes the vital signs, to thus generate the first arithmetically processed signal and transmit the thus-generated first arithmetically processed signal to the output control section 15. The first arithmetically processed signal generated by the first arithmetic processing section 13 corresponds to a signal of the vital sign waveforms 71 to 73 and the numeric data 74 to 78.

The first arithmetic processing section 13 transmits the thus-generated first arithmetically processed signal to the second arithmetic processing section 14. The second arithmetic processing section 14 analyzes and arithmetically processes the thus-received first arithmetically processed signal by means of application software, to thus generate the second arithmetically processed signal, and transmits the thus-generated second arithmetically processed signal to the output control section 15. The second arithmetically processed signal generated by the second arithmetic processing section 13 is a signal pertinent to the vital sign analysis graph 79.

The output control section 15 performs control operation such that the thus-received first arithmetically processed signal is displayed on the window 42 and that the second arithmetically processed signal is displayed on the window 43. The displayed vital sign waveforms 71 to 73 and the numeric data 74 to 78 are monitoring data to be measured at all times. The monitoring data are output from the first arithmetic processing section 13 that runs on the first OS (the embedded OS) 11, whereby the monitoring data can be displayed on the display section 41 without interruption at all times without being affected by the operating state of the second OS (the general purpose OS) 12. Since the second arithmetic processing section 14 runs on the second OS (the general purpose OS) 12 that exhibits high extendability, the second arithmetic processing section 14 further arithmetically processes the first arithmetically processed signal, whereby vital signs having a higher degree of analysis accuracy can be displayed on the display section 41.

The invention is not limited to the configurations that are exemplified in connection with the embodiments and is susceptible to alterations, as appropriate, without departing the gist of the invention.

The vital sign measurement apparatus is equipped with an arithmetic processing section that runs on a first operating system in accordance with operator's input operation and another arithmetic processing section that runs on a second operating system in accordance with operator's input operation and is configured such that an output control section outputs at least any of arithmetically processed signals received from the arithmetic processing sections. Hence, even when a problem occurs in one of the operating systems, the other operating system can measure vital signs without interruption and without being affected by the problem. Moreover, in addition to measuring vital signs by means of the first operating system, vital signs can also be measured by means of the second operating system.

What is claimed is:

1. A vital sign measurement apparatus comprising:
   an input operation section that enables an operator to perform input operation; and
   a housing that houses therein:
      a first operating system;
      a second operating system;
      a first arithmetic processing section configured to run on the first operating system and configured to arithmetically process first vital signs measured by a first measurement section on the basis of an input signal from the input operation section, thereby generating a first arithmetically processed signal;
      a second arithmetic processing section configured to run on the second operating system, configured to be communicable with the first arithmetic processing section, and configured to generate a second arithmetically processed signal on the basis of the input signal from the input operation section by use of the first arithmetically processed signal transmitted from the first arithmetic processing section; and
      an output control section configured to receive the first arithmetically processed signal produced by the first arithmetic processing section and the second arithmetically processed signal produced by the second arithmetic processing section and configured to output at least one of the received arithmetically processed signals,
   wherein the first arithmetic processing section and the second arithmetic processing section are connected through a communication line,
   wherein a level of communication between the first arithmetic processing section and the second arithmetic processing section is limited based on a state of the second operating system, and
   wherein the first arithmetic processing section is further configured to shut off a communication with the second arithmetic processing section when determining that an anomaly occurs in the second operating system in course of the communication with the second arithmetic operating section.

2. The vital sign measurement apparatus according to claim 1, wherein the first arithmetic processing section arithmetically is further configured to process second vital signs measured by a second measurement section on the basis of an input signal from the input operation section, to thus generate the first arithmetically processed signal.

3. The vital sign measurement apparatus according to claim 1, wherein the second arithmetic processing section arithmetically is configured to process second vital signs measured by a second measurement section on the basis of an input signal from the input operation section, to thus generate a second arithmetically processed signal.

4. The vital sign measurement apparatus according to claim 2, further comprising an extension processing section configured to run on the second operating system and configured to analyze or store at least any one of the first vital signs, the second vital signs, the first arithmetically processed signal, and the second arithmetically processed signal.

5. The vital sign measurement apparatus according to claim 1, wherein the second operating system is a general purpose operating system.

6. The vital sign measurement apparatus according to claim 3, wherein the first arithmetic processing section is configured to generate the first arithmetically processed signal by use of the second arithmetically processed signal transmitted from the second arithmetic processing section.

7. The vital sign measurement apparatus according to claim 3, wherein the second measurement section includes an ultrasonic probe.

8. The vital sign measurement apparatus according to claim 3, wherein the second measurement section includes a sensor adapted to be attached to a subject.

9. The vital sign measurement apparatus according to claim 3, wherein the second measurement section is configured to measure an electrocardiogram signal.

10. The vital sign measurement apparatus according to claim 3, wherein the second measurement section is configured to measure an electroencephalogram signal or a signal pertinent to an electroencephalogram test.

11. The vital sign measurement apparatus according to claim 3, wherein the second measurement section is configured to measure an electromyogram signal and an evoked potential signal.

12. A vital sign measurement apparatus comprising:
an input operation section that enables an operator to perform input operation; and
a housing that houses therein:
a first operating system;
a second operating system;
a first arithmetic processing section configured to run on the first operating system and configured to arithmetically process first vital signs measured by a first measurement section on the basis of an input signal from the input operation section, thereby generating a first arithmetically processed signal;
a second arithmetic processing section configured to run on the second operating system, configured to be communicable with the first arithmetic processing section, and configured to generate a second arithmetically processed signal on the basis of the input signal from the input operation section by use of the first arithmetically processed signal transmitted from the first arithmetic processing section; and
an output control section configured to receive the first arithmetically processed signal produced by the first arithmetic processing section and the second arithmetically processed signal produced by the second arithmetic processing section and configured to output at least one of the received arithmetically processed signals,
wherein the first arithmetic processing section and the second arithmetic processing section are connected through a communication line,
wherein a level of communication between the first arithmetic processing section and the second arithmetic processing section is limited based on a state of the second operating system, and
wherein the level of communication between the first arithmetic processing section and the second arithmetic processing section is partially blocked upon detection of the state of the second operating system being a cessation of the second operating system.

13. The vital signs measurement apparatus according to claim 1, wherein the first arithmetic processing section controls the limiting of the level of communication.

14. The vital signs measurement apparatus according to claim 12, wherein the first arithmetic processing section controls the partial blocking of the level of communication.

15. A vital sign measurement apparatus comprising:
an input operation section that enables an operator to perform input operation; and
a housing that houses therein:
a first operating system;
a second operating system;
an input control section that is connected to the input operation section and that converts an operation signal input from the input operation section into a control signal;
a first arithmetic processing section that is connected to the input control section through a first communication line, the first arithmetic processing section being configured to run on the first operating system and being configured to arithmetically process first vital signs measured by a first measurement section on the basis of the control signal, thereby generating a first arithmetically processed signal;
a second arithmetic processing section that is connected to the input control section through a second communication line, the second arithmetic processing section being configured to run on the second operating system, being communicable with the first arithmetic processing section, and being configured to generate a second arithmetically processed signal on the basis of the control signal by use of the first arithmetically processed signal transmitted from the first arithmetic processing section; and
an output control section configured to receive the first arithmetically processed signal produced by the first arithmetic processing section and the second arithmetically processed signal produced by the second arithmetic processing section and configured to output at least one of the received arithmetically processed signals,
wherein, when the second arithmetic processing section is in a normal operation, the output control section is configured to receive the first arithmetically processed signal and the second arithmetically processed signal, and is configured to output both of the first arithmetically processed signal and the second arithmetically processed signal, and wherein, when the second arithmetic processing section becomes inoperative, the control signal from the input control section is transmitted to the first arithmetic processing section through the first communication line, the first arithmetic processing section is configured to generate the first arithmetically processed signal on the basis of the control signal, and the output control section is configured to receive and output the first arithmetically processed signal.

16. The vital sign measurement apparatus according to claim 15, wherein:

the first arithmetic processing section and the second arithmetic processing section are connected through a third communication line, the control signal transmitted from the input control section to the first arithmetic processing section through the first communication line is identical with the control signal transmitted from the first arithmetic processing section to the second arithmetic processing section through the third communication line.

* * * * *